United States Patent
Al-Ali

(10) Patent No.: US 11,376,408 B2
(45) Date of Patent: *Jul. 5, 2022

(54) PRESSURE-SENSING BLEED-BACK CONTROL VALVE WITH IMPROVED SEALING

(71) Applicant: Cygnus Medical LLC, Akron, OH (US)

(72) Inventor: Firas Al-Ali, Hudson, OH (US)

(*) Notice: Subject to any disclaimer, the term of this patent is extended or adjusted under 35 U.S.C. 154(b) by 146 days.

This patent is subject to a terminal disclaimer.

(21) Appl. No.: 16/784,735

(22) Filed: Feb. 7, 2020

(65) Prior Publication Data
US 2020/0188650 A1  Jun. 18, 2020

Related U.S. Application Data

(63) Continuation-in-part of application No. 15/782,664, filed on Oct. 12, 2017, now Pat. No. 10,625,067.
(Continued)

(51) Int. Cl.
*A61M 39/06* (2006.01)
*A61M 25/00* (2006.01)

(52) U.S. Cl.
CPC ........ *A61M 39/06* (2013.01); *A61M 25/0021* (2013.01); *A61M 2039/062* (2013.01); *A61M 2039/0686* (2013.01); *A61M 2210/12* (2013.01)

(58) Field of Classification Search
CPC ............ A61M 39/06; A61M 2039/062; A61M 2039/064; A61M 2039/0666; A61M 2039/0646; A61M 2039/0686
(Continued)

(56) References Cited

U.S. PATENT DOCUMENTS 165,756 A  7/1875 Richter et al.
318,881 A  5/1885 de Susini
(Continued)

FOREIGN PATENT DOCUMENTS

CA  2682474 A1  7/2008
CA  2974544 A1  12/2016
(Continued)

OTHER PUBLICATIONS

Sense-IT (DIPT). Product Literature (PDF) [online]. Elcam Medical, Oct. 2018 [retrieved on Jul. 14, 2020]. Unique identification No. <REV-7 Oct. 2018 ISO 13485>. Retrieved from the Internet: <URL: https://www.elcam-medical.com/sites/elcam/UserContent/files/Sense-IT_DIPT_ENG_REV7_10-2018.pdf>.
(Continued)

*Primary Examiner* — Bhisma Mehta
*Assistant Examiner* — Nidah Hussain
(74) *Attorney, Agent, or Firm* — Dominic A. Frisina

(57) ABSTRACT

A novel seal is provided along with a valve for implementing the seal in the form of a hemostatic catheterization valve. A pressure-sensing form of the hemostatic valve is also provided. The novel seal includes a pair of cooperating conical gaskets divided through their apexes into a plurality of edge-abutting semi-conical flaps. The seals are angularly fixed in orientation relative to each other using registering structures such as complementary tabs and sockets. More specifically, the seams where the semi-conical flaps abut are angularly off-set between the two conical gaskets by a predetermined amount.

20 Claims, 3 Drawing Sheets

Related U.S. Application Data

(60) Provisional application No. 62/407,258, filed on Oct. 12, 2016.

(58) Field of Classification Search
USPC .................................. 604/167.04, 167.03
See application file for complete search history.

(56) References Cited

U.S. PATENT DOCUMENTS

| | | | |
|---|---|---|---|
| 3,865,100 A | 2/1975 | Kanai et al. | |
| 4,160,448 A | 7/1979 | Jackson | |
| 4,334,160 A | 6/1982 | McCarty | |
| 4,407,298 A | 10/1983 | Lentz et al. | |
| 4,545,389 A | 10/1985 | Schaberg et al. | |
| 4,587,975 A | 5/1986 | Salo et al. | |
| 4,842,591 A | 6/1989 | Luther | |
| 5,256,149 A * | 10/1993 | Banik | A61B 17/3421 604/164.01 |
| 5,342,315 A * | 8/1994 | Rowe | A61B 17/3462 604/167.06 |
| 5,358,490 A | 10/1994 | Henry et al. | |
| 5,383,896 A | 1/1995 | Gershony et al. | |
| 5,626,601 A | 5/1997 | Gershony et al. | |
| 5,868,778 A | 2/1999 | Gershony et al. | |
| 5,911,710 A | 6/1999 | Barry et al. | |
| 5,951,583 A | 9/1999 | Jensen et al. | |
| 5,957,952 A | 9/1999 | Gershony et al. | |
| 6,017,359 A | 1/2000 | Gershony et al. | |
| 6,033,366 A | 3/2000 | Brockway et al. | |
| 6,083,207 A | 7/2000 | Heck | |
| 6,287,280 B1 | 9/2001 | Lampropoulos et al. | |
| 6,296,658 B1 | 10/2001 | Gershony et al. | |
| 6,331,176 B1 | 12/2001 | Becker et al. | |
| 6,379,308 B1 | 4/2002 | Brockway et al. | |
| 6,488,674 B2 | 12/2002 | Becker et al. | |
| 6,511,434 B1 | 1/2003 | Haytman et al. | |
| 6,551,283 B1 * | 4/2003 | Guo | A61M 39/06 251/149.1 |
| 6,575,960 B2 | 6/2003 | Becker et al. | |
| 6,695,820 B1 | 2/2004 | Armstrong et al. | |
| 6,709,418 B1 * | 3/2004 | Aboul-Hosn | A61M 1/3666 604/167.03 |
| 6,896,002 B2 | 5/2005 | Hart et al. | |
| 7,025,727 B2 | 4/2006 | Brockway et al. | |
| 7,347,822 B2 | 3/2008 | Brockway et al. | |
| 7,938,809 B2 | 5/2011 | Lampropoulos et al. | |
| 7,976,503 B2 | 7/2011 | Khan et al. | |
| 8,048,032 B2 | 11/2011 | Root et al. | |
| 8,142,413 B2 | 3/2012 | Root et al. | |
| 8,246,585 B2 | 8/2012 | Schennib | |
| 8,292,850 B2 | 10/2012 | Root et al. | |
| 8,852,147 B2 | 10/2014 | Callan et al. | |
| RE45,380 E | 2/2015 | Root et al. | |
| RE45,760 E | 10/2015 | Root et al. | |
| RE45,776 E | 10/2015 | Root et al. | |
| RE46,116 E | 8/2016 | Root et al. | |
| 9,675,792 B2 * | 6/2017 | Bramwell | A61M 39/0606 |
| 9,895,524 B2 | 2/2018 | Lareau | |
| 10,939,831 B2 | 3/2021 | Al-Ali | |
| 2004/0243044 A1 | 12/2004 | Penegor et al. | |
| 2005/0096605 A1 * | 5/2005 | Green | A61M 39/06 604/246 |
| 2007/0038143 A1 | 2/2007 | Christensen et al. | |
| 2007/0260219 A1 | 11/2007 | Root et al. | |
| 2008/0171988 A1 | 7/2008 | Blanco | |
| 2009/0204078 A1 | 8/2009 | Mitchell et al. | |
| 2009/0318881 A1 | 12/2009 | Shennib | |
| 2010/0324567 A1 | 12/2010 | Root et al. | |
| 2012/0165756 A1 | 6/2012 | Root et al. | |
| 2016/0066932 A1 | 3/2016 | Root et al. | |
| 2016/0346515 A1 | 12/2016 | Buller et al. | |
| 2017/0050003 A1 | 2/2017 | Root et al. | |

FOREIGN PATENT DOCUMENTS

| | | |
|---|---|---|
| WO | 2016040579 A1 | 3/2016 |
| WO | 2016191415 A1 | 12/2016 |

OTHER PUBLICATIONS

Y-Click. Product Literature (PDF) [online]. Elcam Medical, Oct. 2018 [retrieved on Jul. 14, 2020]. Unique identification No. <REV-6 Oct. 2018 ISO 13485>. Retrieved from the Internet: <URL: https://www.elcam-medical.com/sites/elcam/UserContent/files/Y-Click_REV6_10-2018_v4.pdf>.

Guardian II Hemostasis Valve. Product Brochure (PDF) [online]. Vascular Solutions, Inc., Sep. 2019 [retrieved on Jul. 14, 2020]. Unique identification No. <MC-005917 Rev>. Retrieved from the Internet: <URL: https://www.teleflex.com/usa/en/product-areas/interventional/coronary-interventions/guardian-ii-hemostasis-valve/Guardian-Hemostasis-Valve-Brochure_MC-005917-r0.pdf>.

SafeSheath Sealing Adapter. Product Sheet (PDF) [online]. Pressure Products Medical Supplies, Inc. [retrieved on Jul. 14, 2020]. Retrieved from the Internet: <URL: http://www.pressure-products.com/Downloads/PS/SA_PS.pdf>.

* cited by examiner

PRESSURE-SENSING BLEED-BACK CONTROL VALVE WITH IMPROVED SEALING

This application is a continuation-in-part of pending U.S. patent application Ser. No. 15/782,664 filed Oct. 12, 2017 which claims the benefit of U.S. provisional patent application No. 62/407,258 filed Oct. 12, 2016. This application incorporates by reference application Ser. Nos. 15/782,664 and 62/407,258 in their entirety.

I. BACKGROUND OF THE INVENTION

A. Field of Invention

The present invention generally relates to the field bleed-back control valves used in medical catheterization procedures.

B. Description of the Related Art

Bleed-back control valves are well-known and have long been in use in surgical intervention and diagnostic procedures involving catheters. They are alternatively known as backflow control valves and hemostasis valves. One common bleed-back control valve is the Tuohy-Borst adapter. In general terms, a catheter is fed into the adapter through an upstream catheter access port, it travels through the lumen of the adapter, and exits through another port at the downstream end, thus entering the patient.

Tuohy-Borst adapters include a threaded fitting containing a compressible cylindrical gasket. As the gasket is axially compressed by the fitting it collapses around the catheter locking it in place and preventing blood or other fluids from backflowing through the catheter access port. The typical mode of using a Tuohy-Borst adapter is to feed a catheter through the adapter to position it within a patient. Once positioned, the catheter is locked in place.

The Tuohy-Borst adapter is a very common tool in the medical profession even to the extent of being a standard; however, this tool has certain shortcomings. For instance, bleed-back can only be stopped when the catheter is locked in place. Therefore, as the physician is positioning the catheter within a patient, blood will backflow to some extent. This creates a blood spill, which is undesirable because it increases the risk of exposure to blood-borne pathogens, and because blood loss can have negative consequences for the patient. Generally, the physician will loosen the catheter just enough to allow the catheter to slide. This tends to limit bleed-back, but it does not eliminate it.

What is needed is a bleed-back control valve that slideably engages a catheter while simultaneously blocking bleed-back. Some embodiments of the present invention may provide one or more benefits or advantages over the prior art.

II. SUMMARY OF THE INVENTION

Some embodiments may relate to a seal for a bleed-back control valve. The seal may comprise a downstream conical gasket having a conical wall comprising an apex at a downstream end and a base flange at an upstream end. The conical wall may be divided through the apex into a plurality of edge-abutting semi-conical flaps, the base flange having at least one registering structure disposed on an upstream surface of the downstream conical gasket. The seal may also comprise an upstream conical gasket having a conical wall comprising an apex at a downstream end and a base flange at an upstream end. The conical wall may be divided through the apex into a plurality of edge-abutting semi-conical flaps. The base flange may have at least one registering structure disposed on a downstream surface of the upstream conical gasket complementary to, and thus adapted to engage, the at least one registering structure disposed on an upstream surface of the downstream conical gasket. The at least one registering structure of the upstream conical gasket is angularly off-set from the at least one registering structure of the downstream conical gasket by a predetermined amount.

According to some embodiments the at least one registering structure of the upstream conical gasket and the at least one registering structure of the downstream conical gasket each comprise either at least one register tab or at least one register socket such that the at least one register tab is receivable by the at least one register socket, fixing the angular orientation of the upstream conical gasket relative to the downstream conical gasket.

According to some embodiments the angular off-set is such that a seam between two abutting semi-conical flaps of the downstream conical gasket is off-set from a nearest neighbor seam between two abutting semi-conical flaps of the upstream conical gasket by a predetermined amount.

According to some embodiments the conical walls of the upstream and downstream conical gaskets abut each other when the at least one registering structure of the upstream conical gasket receives, or is received by, the at least one registering structure of the downstream conical gasket.

According to some embodiments the base flanges of the upstream and downstream conical gaskets are simultaneously receivable in a mounting relation by a complementary mounting groove of a valve body.

According to some embodiments the plurality of edge-abutting semi-conical flaps of the upstream and downstream conical seals are elastically spreadable to receive a catheter in a dynamically sealing relation as the catheter moves through the apexes of the upstream and downstream conical seals.

According to some embodiments the plurality of edge-abutting semi-conical flaps of the upstream and downstream conical seals are elastically spreadable to receive a catheter in a statically sealing relation as the catheter is stationarily disposed in the apexes of the upstream and downstream conical seals.

According to some embodiments the at least one registering structure of the upstream and/or downstream conical gasket comprises either a pair of register tabs or a pair of register sockets, the pair being disposed at 180o from each other as measured about the base flange.

According to some embodiments the upstream and/or downstream conical gasket comprises a pair of register tabs on one surface of the base flange and a pair of register sockets on an opposing surface of the base flange.

According to some embodiments n the upstream and downstream conical gaskets are structurally identical.

According to some embodiments the upstream and downstream conical gaskets each include a register tab on one surface of the base flange and a register socket on an opposing surface of the base flange such that the register tab and the register socket are angularly off-set from each other by a predetermined amount.

According to some embodiments the angular off-set is between 1° and 59°, or about 15°+/−5°.

According to some embodiments the upstream and/or downstream conical gasket comprises four or six semi-conical flaps.

Embodiments of the invention may include a valve, comprising a valve body comprising an inner luminal wall extending from an upstream opening to a downstream opening; a downstream conical gasket having a conical wall comprising an apex at a downstream end and a base flange at an upstream end, the conical wall being divided through the apex into a plurality of edge-abutting semi-conical flaps, the base flange having at least one registering structure disposed on an upstream surface of the downstream conical gasket; an upstream conical gasket having a conical wall comprising an apex at a downstream end and a base flange at an upstream end, the conical wall being divided through the apex into a plurality of edge-abutting semi-conical flaps, the base flange having at least one registering structure disposed on a downstream surface of the upstream conical gasket, the at least one registering structure being complementary to, and thus adapted to receive, the at least one registering structure disposed on an upstream surface of the downstream conical gasket, wherein the at least one registering structure of the upstream conical gasket is angularly off-set from the at least one registering structure of the downstream conical gasket by a predetermined amount; a mounting groove in the inner luminal wall sized to simultaneously receive the base flanges of the upstream and downstream conical seals in a mounted relation; and a frustoconical valve seat supportively receiving a downstream surface of the conical wall of the downstream conical gasket, the frustoconical valve seat defining an orifice in fluid communication with a space defined by the inner luminal wall of the valve body, wherein the apex of the downstream conical gasket protrudes through the orifice.

Embodiments may further include a cylindrical seal disposed upstream of both the upstream and downstream conical gaskets, wherein a central through-hole of the cylindrical seal is aligned and in fluid communication with a lumen defined by the inner luminal wall of the valve body.

Embodiments may further include a threaded compression fitting in axially compressive communication with the cylindrical seal such that compression of the cylindrical seal is controllable through turning the threaded compression fitting.

According to some embodiments the central through-hole of the cylindrical seal is sized to slidably receive a catheter in an uncompressed state, and to lockably receive a catheter in a compressed state.

Embodiments may further include a threaded mount fixedly co-operable with a mountable needle.

Embodiments may further include a sidearm flush port in fluid communication with the lumen downstream of the upstream and downstream conical seals.

Embodiments may further include a pressure transducer in pressure communication with a lumen, defined by the inner luminal wall of the valve body, downstream of the downstream conical seal.

Other benefits and advantages will become apparent to those skilled in the art to which it pertains upon reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof, wherein like reference numerals indicate like structure, and wherein.

IV. DETAILED DESCRIPTION OF THE INVENTION

As used herein the terms "embodiment", "embodiments", "some embodiments", "other embodiments" and so on are not exclusive of one another. Except where there is an explicit statement to the contrary, all descriptions of the features and elements of the various embodiments disclosed herein may be combined in all operable combinations thereof.

Language used herein to describe process steps may include words such as "then" which suggest an order of operations; however, one skilled in the art will appreciate that the use of such terms is often a matter of convenience and does not necessarily limit the process being described to a particular order of steps.

Conjunctions and combinations of conjunctions (e.g. "and/or") are used herein when reciting elements and characteristics of embodiments; however, unless specifically stated to the contrary or required by context, "and", "or" and "and/or" are interchangeable and do not necessarily require every element of a list or only one element of a list to the exclusion of others.

The terms upstream and downstream are used herein to indicate the relative position or orientation of parts of an embodiment in an assembled state, and/or while in use. Their meaning will be clear in context to the ordinarily skilled artisan, but in general they refer to the direction of travel of a catheter as it is inserted into an embodiment.

Figure 1A:
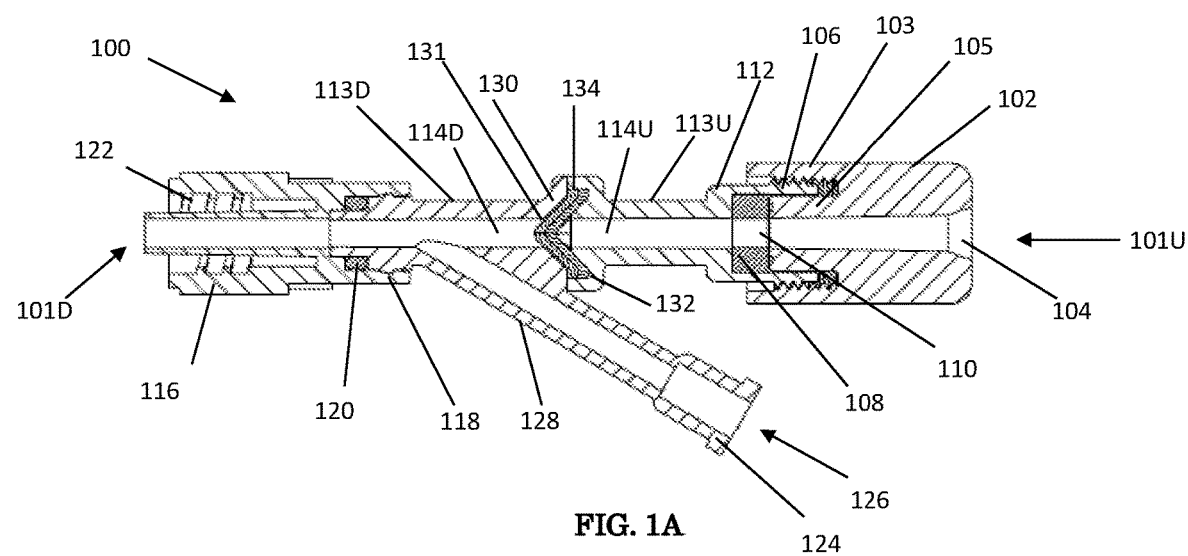
FIG. 1A is a cross sectional view of a valve according to an embodiment of the invention.

Referring now to the drawings wherein the showings are for purposes of illustrating embodiments of the invention only and not for purposes of limiting the same, FIG. 1A is a cross sectional view of an embodiment 100 of the invention comprising a fully assembled bleed-back control valve. The upstream end 101U is shown to the right, and the downstream end 101D is on the left. The upstream end 101U includes a chamfered, or beveled, catheter access port 104 formed in a compression nut 102. The nut 102 has female threads 103 downstream of the access port 104. The nut also includes a plunger 105 that functions to axially compress a cylindrical gasket 108 as the nut 102 is tightened onto a male thread 106 of an upstream portion of the valve body 113U. The cylindrical seal is compressed between the plunger 105 and a seat 112 formed in the valve body 113U. A central through-hole 110 of the cylindrical seal 108 is aligned coaxially with the lumen 114U, 114D which is defined by an inner luminal wall of the valve body 113U, 113D. Thus, a catheter may enter through the access port 104, pass through the through-hole 110, enter the lumen 114U, 114D and exit the valve body at the downstream end 101D of the bleed-back control valve. The central through-hole 110 is sized to slideably receive the catheter in an uncompressed state. In this context, the term slideably receive means that the catheter is free to travel through the central through hole 110 regardless of whether the catheter actually makes sliding contact with the sides of the through-hole 110.

The valve body is divided into two halves, namely an upstream half 113U and a downstream half 113D. The reason for dividing the valve body in this way is to provide structure for easily installing a double conical seal 134 into a mounting groove 132 formed by the two halves. While the present embodiment is divided into two halves, the skilled artisan will readily understand that any of a wide variety of known structures for retaining a seal would also be appropriate as a matter of design choice. Such variations are well within the scope of the present invention as described and claimed herein. FIG. 1A shows a double conical seal 134 held in a mounted relation by the mounting groove 132.

In the embodiment of FIG. 1A, the groove 132 holding the double conical seal has a complex frustoconical-shaped wall 130 formed in the upstream and downstream halves of the valve body 113U, 113D. The frustoconical wall 130 formed in the upstream and downstream halves of the valve body 113U, 113D serves as a valve seat. Thus, the frustoconical wall 130 may also be referred to herein as a frustoconical valve seat 130. In addition to holding the double conical seal 134 in place, this shape also tends to support a portion of the seal 134 while allowing the apex of the seal to protrude through an orifice 131 and into the downstream lumen 114D. This arrangement may be advantageous by, for instance and without limitation, limiting the amount of flexure that the seal experiences during insertion of a catheter and/or providing improved sealing around a catheter by stiffening the seal and thereby increasing sealing force.

With continued reference to FIG. 1A, the downstream valve body 113D terminates in a rotatable collar fitting comprising an annular ridge and groove connection 118 to a standard Luer Lock fitting 116 threaded 122 to fixedly cooperate with cannulas. By fixedly cooperate, it is contemplated that the threads of the Luer Lock fitting may receive a cannula having complementary structure in a fastened and thus fixed relation relative to the Luer Lock fitting. The fitting 116 is sealed with an O-ring 120 to prevent leakage of fluids from the lumen 114D, 114U. Some embodiments, including the one shown in FIG. 1A, may include a sidearm flush 128 with a port 124 co-operable with standard fluid delivery devices such as syringes. The lumen 126 of the sidearm flush is shown in fluid communication with the downstream lumen 114D of the downstream valve body 113D.

Figure 1B:
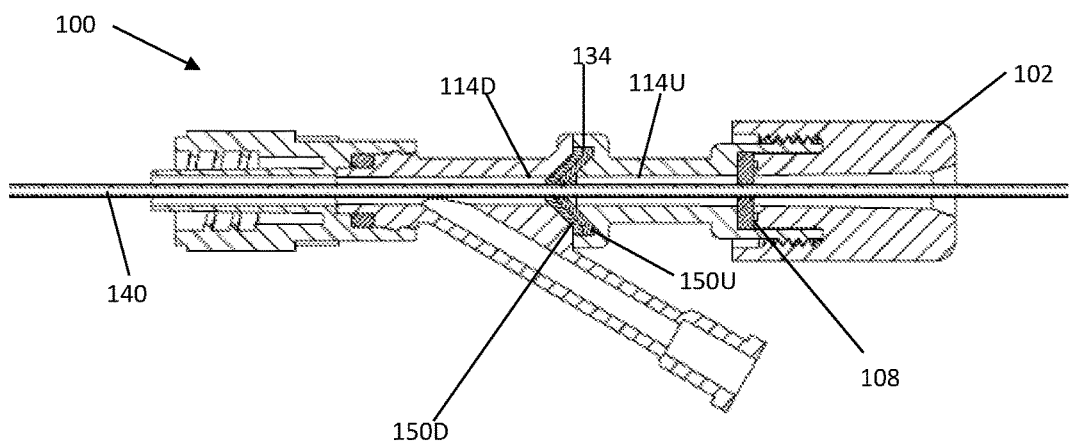
FIG. 1B is a cross sectional view of the valve of FIG. 1A receiving a catheter.

In contrast to FIG. 1A, FIG. 1B illustrates the same embodiment 100 receiving a catheter 140. The catheter is shown locked in place by the cylindrical seal 108 which has been compressed by tightening the nut 102. Accordingly, the seal 108 has collapsed around the catheter 140 and thus locks it in place through friction. FIG. 1B also illustrates the upstream conical gasket 150U and the downstream conical gasket 150D of the double conical seal 134 opening at their apexes to receive the catheter 140. The gaskets 150U, 150D dynamically seal against the catheter 140 as it is inserted into the embodiment 100 and fed into a patient. The gaskets 150U, 150D then statically maintain the seal when the catheter 140 is locked in place, as shown here.

Figure 2:
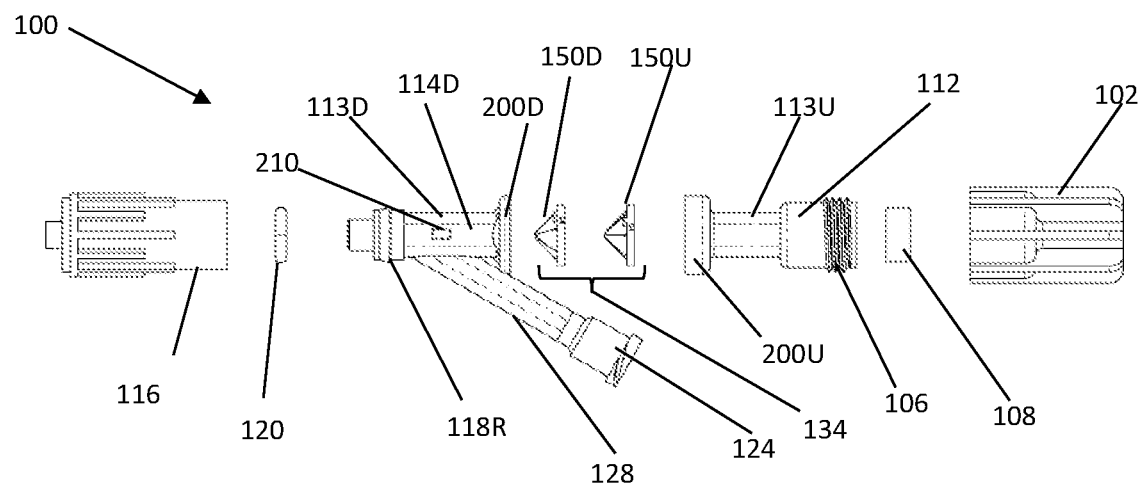
FIG. 2 is an exploded view of the valve of FIGS. 1A and 1B.

FIG. 2 is an exploded view of the embodiment shown in FIGS. 1A and 1B. The valve body is shown divided into its upstream 113U and downstream 113D halves. The upstream valve body 113U includes a seat 112 receiving a cylindrical seal 108. A nut 102 is threaded onto the male thread 106 of the upstream valve body 103U, which compresses the cylindrical seal 108 with a plunger 105 (see FIG. 1A). Interposed between the two halves of the valve body 113U, 113D are two conical gaskets. One is an upstream conical gasket 150U and the other is a downstream conical gasket 150D. The base of the upstream gasket 150U fits into a seat 200 at one end of the upstream valve body 113U. The two gaskets 150U, 150D stack one within the other, and their angular orientation relative to each other is set by registering structures, as will be described in more detail below.

The conical gaskets 150U, 150D are mounted between an upstream flange 200U and a downstream flange 200D. The upstream and downstream flanges 200U, 200D include the frustoconical wall 130 and groove 132 which are not visible in this figure, but which can be seen in FIG. 1A. The downstream end of the downstream valve body 113D terminates in a ridge 118R of the ridge and groove connection 118 shown in FIG. 1A. The ridge 118R receives the Luer Lock collar fitting 116 in a rotatable relation sealed with an O-ring 120.

A pressure transducer 210 is shown mounted within the lumen 114D of the downstream valve body 113D. The transducer advantageously has a thin profile which allows it to be in the lumen without occluding or obstructing. Thus, the transducer cooperates with a catheter 140 in that it does not obstruct its path. Accordingly, the transducer is capable of obtaining real time measurements of body fluid pressures while carrying out a procedure without the need for additional fluidics, and without the need to pause the procedure to measure pressure. Suitable pressure transducers are well known in the art and may be selected as a matter of design choice. Optionally, the transducer 210 may include or communicate with electronic components for wirelessly broadcasting telemetry data. The skilled artisan will appreciate that the placement of the transducer 210 is advantageously within the downstream lumen 114D because the upstream lumen 114U is isolated by the double conical seal 134.

FIGS. 3A through 3E illustrate the same conical gasket 150 in various orientations. The embodiment illustrated in FIGS. 1-2 illustrate a double conical seal 134 which is made of a stacked pair of this conical gasket 150 which, in FIGS. 1-2, are labeled upstream 150U and downstream 150D. Their unique reference numbers 150U and 150D are intended only to indicate their position in the assembled device. In the embodiments illustrated herein, the upstream and downstream conical gaskets are structurally identical to each other and to the gasket illustrated in FIGS. 3A-3E. The skilled artisan will readily appreciate that being identical is not a requirement, but that certain manufacturing efficiencies are gained by having two of a single part rather than two different parts.

With collective reference to FIGS. 3A-3E a conical gasket 150 is shown that has an annular base flange 302. The base flange 302 cooperates with the groove defined in the upstream and downstream flanges 200U, 200D of FIG. 2. The upstream surface of a conical wall 300U and the downstream surface of the same wall 300D are shown divided into six equal semi-conical flaps 304 through the apex 312. The edges of each semi-conical flap 304 abut the edges of its nearest neighbors to form seams 306. As used in this context, the term seam is intended only to denote area where flap edges abut one another, and it is not intended to imply that the edges are joined. To the contrary, the edges are not joined, and thus the flaps 304 can spread apart in response to an impinging catheter to form an opening 320 at the apex 312 where the catheter may pass through.

The circle 310 is not a structural element of the conical gasket 150. Rather, it is intended to indicate the region where the conical wall 300U, 300D begins to curve to form the blunted apex 312 shown most clearly in FIGS. 3B, 3D, and 3E.

Each seam 306 terminates in a circular through-hole 307 near the base flange 302. This structure is optional, but may be advantageous in preventing tearing of the gasket at the seam terminuses. The gasket 150 has a pair of register tabs 308T located on the downstream surface 180 degrees apart from each other. Similarly, the illustrated embodiment includes a pair of register sockets 308S located on the upstream surface 180 degrees apart. Thus, a pair of the gasket 150 may be stacked such that the register tabs 308T of one cooperatively fit into, i.e. engage, the sockets 308S of the other. Conversely, the sockets 308S of one gasket 150 may be said to engage the register tabs 308T of the other gasket 150. Register tabs 308T and register sockets 308S are referred to herein according to their genus as register structures, or registering structures. Thus, the angular orientation of the gaskets relative to each other may be fixed.

When FIGS. 1A and 1B are viewed in connection with FIG. 2, it is clear to the person having ordinary skill in the art that the gaskets 150U and 150D are stacked one within the other. Stated differently, the downstream gasket 150D receives the upstream gasket 150U such that their conical walls abut each other. Furthermore, when the conical walls of the upstream 150U and downstream 150D conical gaskets abut, the registering structures of the respective gaskets must engage each other.

The skilled artisan will readily appreciate that the number and distribution of register tabs and register sockets may vary. Embodiments may have only one register tab 308T and one register socket 308S provided that they are positioned to cooperate with the tabs and sockets of other gaskets 150. Alternatively, embodiments may have a plurality of tabs and sockets, and they may be disposed on either the upstream or downstream surface, or even on both surfaces.

With further regard to FIGS. 3A-3E the register tabs 308T and register sockets 308S of an individual gasket 150 are shown off-set from each other by an angle φ. The precise magnitude of the off-set is not critical; however, it should be sufficient to cause the seams 306 of two stacked gaskets 150 to be sufficiently off-set from each other to allow the semi-conical flaps 304 to elastically spread under normal operating conditions, where the embodiment is sealably receiving a catheter, without causing bleed-back of body fluids into the upstream lumen 114U. Suitable magnitudes will depend in part on the number of semi-conical flaps 304, which may be more or fewer than the illustrated number without departing from the scope of the invention. The skilled artisan will appreciate that a greater number of flaps 304 requires more seams 306 which requires smaller angular off-sets. Suitable magnitudes for φ according to the illustrated embodiment include any angle from 1° to 59°. Other ranges within the scope of the invention include 1° to 5°, 5° to 10° 10° to 15° 15° to 20° 20° to 25° 25° to 30° 30° to 35° 35° to 40°, 40° to 45°, 45° to 50°, 50° to 55°, 55° to 59°, or any combination thereof.

Figure 3A:
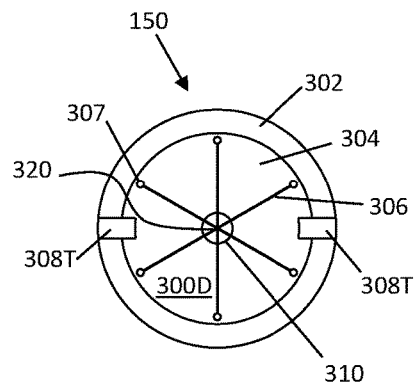
FIG. 3A is a top view of a conical gasket according to an embodiment of the invention.
Figure 3B:
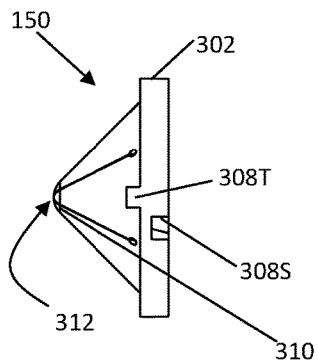
FIG. 3B is a side view of the conical gasket of FIG. A.
Figure 3C:
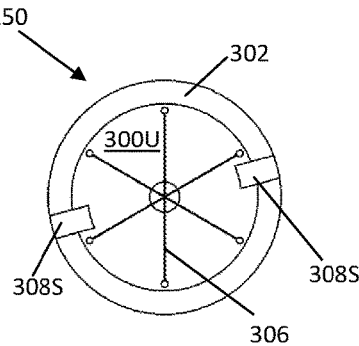
FIG. 3C is a bottom view of the conical gasket of FIG. A.
Figure 3D:
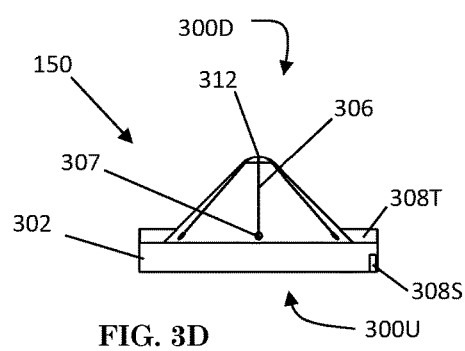
FIG. 3D is a second side view of the conical gasket of FIG. A.
Figure 3E:
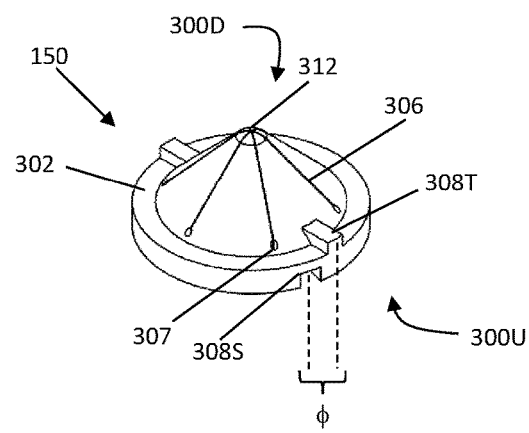
FIG. 3E is an elevation view of the conical gasket of FIG. A.
Figure 3F:
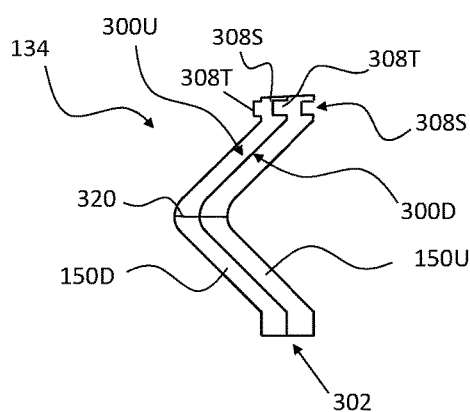
FIG. 3F is a cross sectional view of a double conical seal combining two conical gaskets.

With particular regard to FIG. 3F, a cross sectional view of a double conical seal 134 is shown comprising an upstream conical gasket 150U and a downstream conical gasket 150D. The cross section is taken so as to show the registering socket 308S of the downstream conical gasket 150D receiving, i.e. engaging, the registering tab 308T of the upstream conical gasket 150U. As shown, the upstream conical wall 300U of the downstream conical gasket 150D abuts the downstream conical wall 300D of the upstream conical gasket when the registering structures, namely the registering tab and registering socket, of the respective conical gaskets engage each other. The registering socket 308S and tab 308T are shown as part of the annular base flange 302. This view also shows that the openings 320 of the upstream and downstream conical gaskets 150U, 150D are aligned.

It will be apparent to those skilled in the art that the above methods and apparatuses may be changed or modified without departing from the general scope of the invention. The invention is intended to include all such modifications and alterations insofar as they come within the scope of the appended claims or the equivalents thereof.

I claim:

1. A seal for a bleed-back control valve, comprising:
a downstream conical gasket having a conical wall comprising a blunted apex at a downstream end and a base flange at an upstream end, the conical wall of the downstream conical gasket being divided through the blunted apex of the downstream conical gasket into a plurality of edge-abutting semi-conical flaps defining seams, the base flange having at least one first registering structure disposed on an upstream surface of the downstream conical gasket; and
an upstream conical gasket having a conical wall comprising a blunted apex at a downstream end and a base flange at an upstream end, the conical wall of the upstream conical gasket being divided through the blunted apex of the upstream conical gasket into a plurality of edge-abutting semi-conical flaps defining seams, the base flange of the upstream conical gasket having at least one second registering structure disposed on a downstream surface of the upstream conical gasket complementary to, and thus adapted to engage, the at least one first registering structure disposed on the upstream surface of the downstream conical gasket, wherein the seams of the upstream conical gasket are angularly off-set from the seams of the downstream conical gasket by a predetermined amount.

2. The seal of claim 1, wherein the engagement of the at least one first registering structure and the at least one second registering structure fixes the angular off-set of the seams of the upstream conical gasket relative to the seams of the downstream conical gasket.

3. The seal of claim 1, wherein the conical walls of the upstream and downstream conical gaskets abut each other when the at least one second registering structure of the upstream conical gasket engages the at least one first registering structure of the downstream conical gasket.

4. The seal of claim 1, wherein the base flanges of the upstream and downstream conical gaskets are simultaneously receivable in a mounting relation by a complementary mounting groove of a valve body.

5. The seal of claim 1, wherein the plurality of edge-abutting semi-conical flaps of the upstream and downstream conical gaskets are elastically spreadable to receive a catheter in a dynamically sealing relation as the catheter moves through the apexes of the upstream and downstream conical gaskets.

6. The seal of claim 1, wherein the plurality of edge-abutting semi-conical flaps of the upstream and downstream conical gaskets are elastically spreadable to receive a catheter in a statically sealing relation as the catheter is stationarily disposed in the apexes of the upstream and downstream conical gaskets.

7. The seal of claim 1, wherein the upstream and downstream conical gaskets are structurally identical.

8. The seal of claim 7, wherein the upstream conical gasket includes the at least one registering structure having a register tab on one surface of the base flange of the upstream conical gasket and the at least one registering structure having a register socket on an opposing surface of the base flange of the upstream conical gasket such that the register tab and the register socket are angularly off-set from each other by a predetermined amount.

9. The seal of claim 8, wherein the angular off-set is between 1° and 59°, or about 15°+/−5°.

10. The seal of claim 1, wherein the plurality of edge-abutting semi-conical flaps of the upstream and/or downstream conical gaskets each comprise four or six semi-conical flaps.

11. The seal of claim 1, wherein each seam terminates in a circular through-hole.

12. The seal according to claim 1, wherein the at least one first registering structure comprises two registering structures, wherein one of the two first registering structures is a registering tab, and one of the two first registering structures is a socket.

13. The seal according to claim 1, wherein the at least one second registering structure comprising two registering structures, wherein one of the two second registering structures is a registering tab, and one of the two second registering structures is a socket.

14. A valve, comprising:
a valve body comprising an inner luminal wall extending from an upstream opening to a downstream opening;
a downstream conical gasket having a conical wall comprising a blunted apex at a downstream end and a base flange at an upstream end, the conical wall of the downstream conical gasket being divided through the blunted apex of the downstream conical gasket into a plurality of edge-abutting semi-conical flaps defining seams, the base flange having at least one first registering structure disposed on an upstream surface of the downstream conical gasket;
an upstream conical gasket having a conical wall comprising a blunted apex at a downstream end and a base flange at an upstream end, the conical wall of the upstream conical gasket being divided through the blunted apex of the upstream conical gasket into a plurality of edge-abutting semi-conical flaps defining seams, the base flange of the upstream conical gasket having at least one second registering structure disposed on a downstream surface of the upstream conical gasket complementary to, and thus adapted to engage, the at least one first registering structure disposed on the upstream surface of the downstream conical gasket, wherein the seams of the upstream conical gasket are angularly off-set from the seams of the downstream conical gasket by a predetermined amount;
a mounting groove in the inner luminal wall sized to simultaneously receive the base flanges of the upstream and downstream conical gaskets in a mounted relation; and
a frustoconical valve seat supportively receiving a downstream surface of the conical wall of the downstream conical gasket, the frustoconical valve seat defining an orifice in fluid communication with a space defined by the inner luminal wall of the valve body, wherein the blunted apex of the downstream conical gasket protrudes through the orifice.

15. The valve of claim 14, further comprising a cylindrical seal disposed upstream of both the upstream and downstream conical gaskets, wherein a central through-hole of the cylindrical seal is aligned and in fluid communication with a lumen defined by the inner luminal wall of the valve body.

16. The valve of claim 15, further comprising a threaded compression fitting in axially compressive communication with the cylindrical seal such that compression of the cylindrical seal is controllable through turning the threaded compression fitting.

17. The valve of claim 16, wherein the central through-hole of the cylindrical seal is sized to slidably receive a catheter in an uncompressed state, and to lockably receive a catheter in a compressed state.

18. The valve of claim 17, further comprising a threaded mount fixedly co-operable with a mountable needle.

19. The valve of claim 18, further comprising a sidearm flush port in fluid communication with a portion of the lumen which is downstream of the upstream and downstream conical gaskets.

20. The valve of claim 14, further comprising a pressure transducer in pressure communication with a lumen, defined by the inner luminal wall of the valve body, downstream of the downstream conical gasket.

* * * * *